United States Patent
Von Alfthan et al.

(10) Patent No.: US 8,151,632 B2
(45) Date of Patent: Apr. 10, 2012

(54) METHOD FOR DEFINING ELEMENT CONTENT AND/OR MINERAL CONTENT

(75) Inventors: Christian Von Alfthan, Espoo (FI); Kari Saloheimo, Espoo (FI)

(73) Assignee: Outotec Oyj, Espoo (FI)

( * ) Notice: Subject to any disclaimer, the term of this patent is extended or adjusted under 35 U.S.C. 154(b) by 94 days.

(21) Appl. No.: 12/097,592

(22) PCT Filed: Dec. 19, 2006

(86) PCT No.: PCT/FI2006/000412
§ 371 (c)(1), (2), (4) Date: Jun. 16, 2008

(87) PCT Pub. No.: WO2007/071811
PCT Pub. Date: Jun. 28, 2007

(65) Prior Publication Data
US 2008/0307902 A1    Dec. 18, 2008

(30) Foreign Application Priority Data
Dec. 21, 2005 (FI) ...................................... 20051308

(51) Int. Cl.
*G01N 11/00* (2006.01)
(52) U.S. Cl. ...................................... 73/53.01
(58) Field of Classification Search .................. 73/53.01
See application file for complete search history.

(56) References Cited

U.S. PATENT DOCUMENTS

| | | | | |
|---|---|---|---|---|
| 3,614,231 A | * | 10/1971 | Shaw | 356/37 |
| 3,628,139 A | * | 12/1971 | Huber | 73/28.01 |
| 4,559,134 A | * | 12/1985 | Wasson | 209/166 |
| 5,795,506 A | * | 8/1998 | Hodosawa et al. | 73/865.5 |
| 2003/0157731 A1 | * | 8/2003 | Yguerabide et al. | 436/523 |
| 2005/0070642 A1 | * | 3/2005 | Kierkels et al. | 524/100 |

FOREIGN PATENT DOCUMENTS

| DE | 3634410 | 4/1988 |
|---|---|---|
| DE | 3704736 | 4/1988 |
| FI | 102015 | 5/1997 |
| JP | 61162734 | 7/1986 |

* cited by examiner

*Primary Examiner* — Hezron E Williams
*Assistant Examiner* — Alex Devito
(74) *Attorney, Agent, or Firm* — Chernoff, Vilhauer, McClung & Stenzel

(57) ABSTRACT

The invention relates to a method for defining particle and/or mineral content in real time in a mineral separation process from finely divided particle material flowing either in solid or slurry-like form, so that from the particle material, there is extracted a representative sample, which sample is then subjected to grain size analysis, on the basis of which there is calculated the element and/or mineral content of the particle material.

23 Claims, 2 Drawing Sheets

METHOD FOR DEFINING ELEMENT CONTENT AND/OR MINERAL CONTENT

Figure 1:
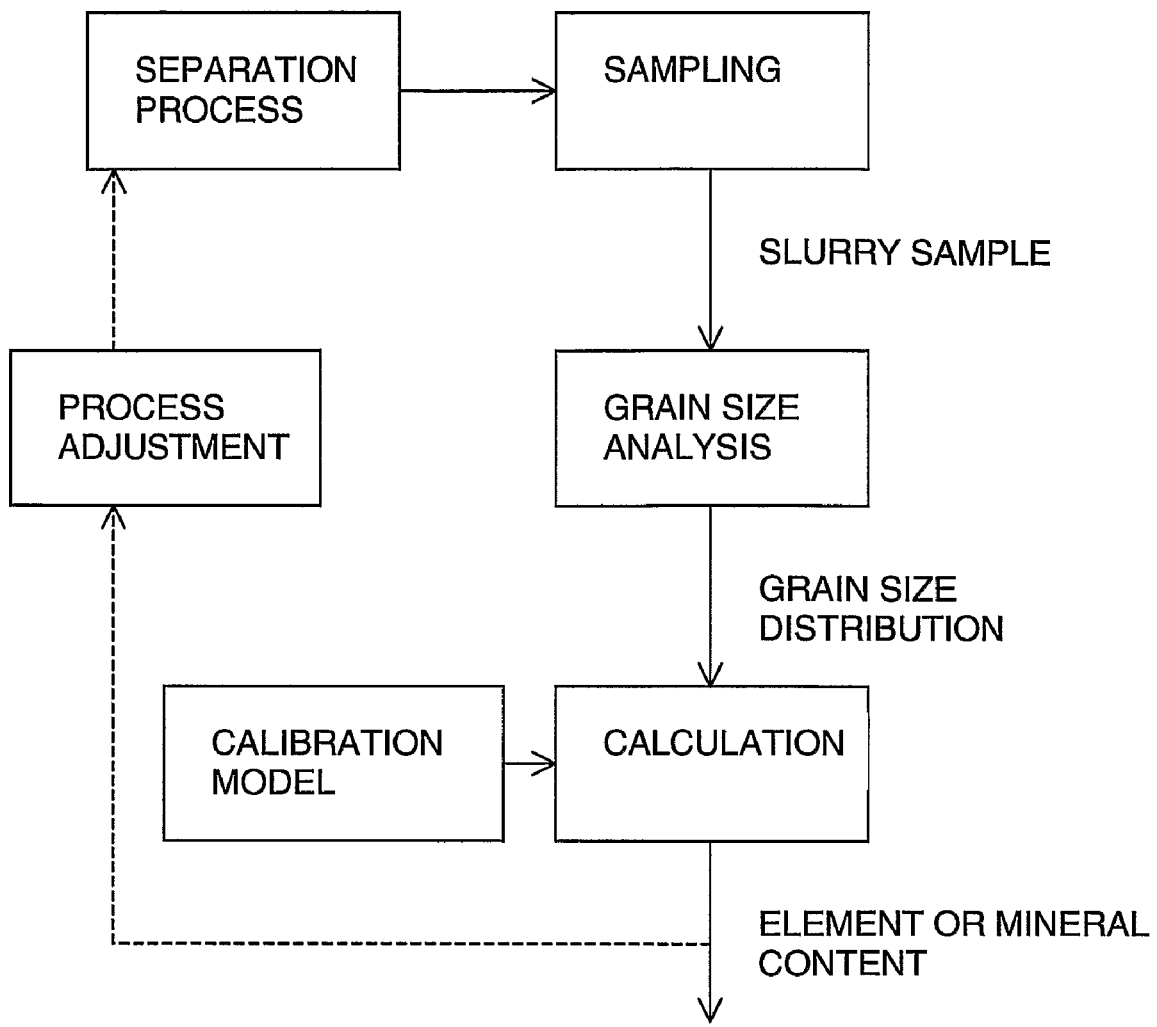

This is a national stage application filed under 35 USC 371 based on International Application No. PCT/FI2006/000412 filed Dec. 19, 2006, and claims priority under 35 USC 119 of Finnish Patent Application No. 20051308 filed Dec. 21, 2005.

The present invention relates to a method for defining particle and/or mineral contents in real time in a mineral separation process from finely divided particle material flowing in either solid or slurry-like form.

In the concentration of minerals, the material obtained from a mine is first made finer by crushing and grinding, so that the valuable minerals contained in the ore are present as separate grains. In mineral separation processes, valuable minerals are recovered as concentrate for further refining. Typically the separation process is flotation, gravity separation, magnetic separation or electrostatic separation, or a combination of these.

In controlling separation processes, there is generally needed real-time measurement data as regards the element and/or mineral contents of the various material flows in the process. On the basis of concentrate content measurements, there is typically ensured that the process produces a product with an optimal quality with respect to further refining. On the basis of the contents of the separation process feed, it is possible to make preliminary adjustments, and on the basis of the measurements of waste flow contents, it is ensured that the process operates with an optimal yield. Separation often includes internal circulation and several different process steps, in which case the measuring of the various intermediate products is necessary for the process control.

Measurements of process material flows are known to be realized with online analyzers. The commonest method for analyzing element contents in mineral processes is X-Ray fluorescence. From the publication FI 51872, there is known a device for analyzing moving solid or pulverous material according to the X-Ray fluorescence principle. When applying said principle there are, however, remarkable restrictions caused by the method. In practice, with wet processes, a measurement carried out directly from the mineral slurry is with the required level of precision possible for certain elements only. The measurement of lighter elements is successful only with complicated sample processing methods that are both sensitive to interference and expensive to realize, in which methods the slurry sample is typically dried, ground finer and briquetted for the analysis. Respectively, in dry mineral processes, X-Ray fluorescence in practice works reliably with directly processed material only with elements heavier than silicon.

With respect to the controlling of separation processes, it often is important to measure the contents of light-weight elements as well. For example the contents of magnesium, silicon, phosphorus and sulfur are important indicators of impurities in the concentrates. From the point of view of process control, in certain separation processes it would also be important to measure mineral contents instead of element contents; for instance in the concentration of serpentinized nickel ores, it is essential for the process control to know, in addition to the magnesium content of the concentrate, whether the magnesium contained in the concentrate is obtained from soapstone or other serpentinite minerals.

In the online measurement of the contents of light-weight elements and minerals, it is known to apply for example Prompt Gamma Neutron Activation Analysis (PGNAA). In that case the measurement is carried out directly from slurry or dry matter. Accuracy often remains modest, or the duration of the measurement becomes immoderately long. In order to get sufficient gammma pulses from the sample, the measurement must be applied to a large sample volume, but the maintenance of said large volume in suspension makes the slurry measurement more difficult. Owing to radiation safety standards, the equipment becomes expensive and difficult to maintain and keep up.

In addition, for example X-Ray Diffraction (XRD) is known to be applied in the online measurement of element and mineral contents; in this case the analysis can be made directly from the slurry or dry matter. Among other applications, let us point out content measurement methods based on optical spectroscopy and nuclear magnetic resonance, which methods are characterized by high expenses, sample match problems, slowness and poor analytic accuracy of the measurement as well as problems connected to repeatability.

The object of the present invention is to eliminate drawbacks of the prior art and to realize an improved method for defining particle and/or mineral contents in real time from finely divided particle material flowing either in solid or slurry-like form, so that for defining the particle and/or mineral content, there is utilized the grain size distribution obtained from the particle material through grain size analysis. The essential novel features of the invention are apparent from the appended claims.

The method according to the invention has several advantages. The invention relates to a method for defining particle and/or mineral contents in real time in a mineral separation process from finely divided particle material, flowing either in solid or slurry-like form, so that from the particle material, there is taken a representative sample, which sample is subjected to grain size analysis, by means of which there is calculated the element and/or mineral content of the particle material. Further, according to a preferred embodiment of the invention, on the basis of grain size analysis, there is defined the grain size distribution, where the value of the cumulative grain size distribution is described as a function of the grain size; on the basis of this, the element and/or mineral content is mathematically calculated by utilizing-constants describing the properties of said element or mineral, defined by calibration. The information obtained from grain size distribution can be used for defining element and/or mineral content from the process feed, product or side product in a mineral separation process, and this data can be utilized in the process control.

According to an embodiment of the invention, grain size distribution is defined by methods based on X-Ray diffraction. According to another embodiment of the invention, grain size distribution is defined by a method based on ultrasonic absorption. According to another embodiment of the invention, grain size distribution is defined by a method based on optical image analysis. According to the invention, on the basis of defining in real time the particle and/or mineral content of finely divided particle material flowing in solid or slurry-like form, a mineral separation process is controlled for producing an optimal feed, product or side product. According to an embodiment of the invention, the mineral separation process is flotation. According to another embodiment of the invention, the separation process is gravity separation. According to yet an embodiment of the invention, the separation process is magnetic separation. According to an embodiment of the invention, the separation process is electrostatic separation. According to an embodiment of the invention, the separation process is classification.

Figure 2A:
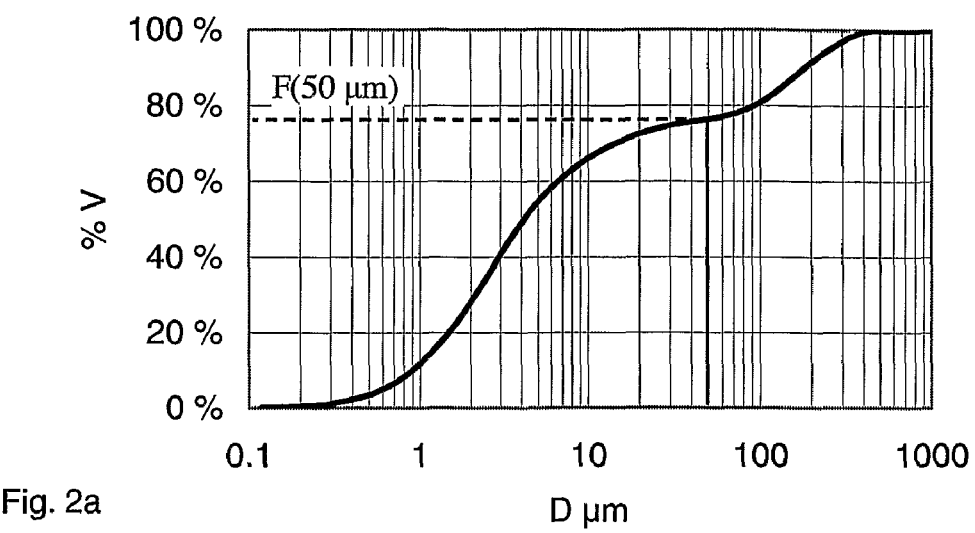
Figure 2B:
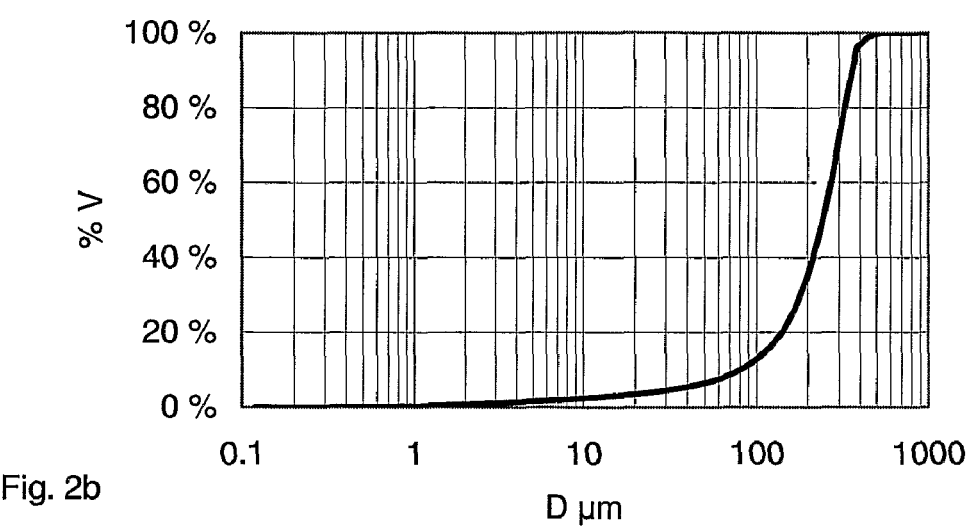
Figure 2C:
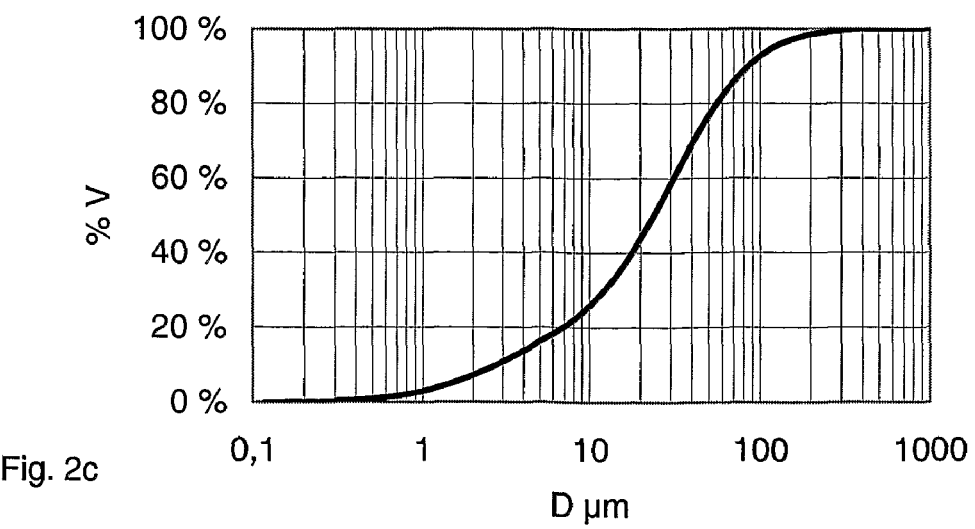

The invention is described in more detail with reference to the accompanying drawings, where FIG. 1 illustrates the invention by way of a process diagram; and FIGS. 2a, 2b and 2c illustrate an example according to the invention.

FIG. 1 illustrates a method according to the invention by way of a process diagram. From the feed, product or waste of a mineral separation process, there is extracted a representative sample in a known way, for example by extracting a sample in two steps from a flowing slurry flow. On the basis of the sample, there is made a grain size analysis describing the grain size of the particles contained in the particle material flowing in the process. The sample can be extracted at desired intervals while the process is going on, either from the feed, product or waste. Data concerning a certain content for the needs of process control is available in real time, i.e. nearly immediately, with allowance for delay times in the calculation. The obtained samples are processed to get a grain size distribution by a method based for instance on ultrasonic absorption, laser diffraction or optical image analysis. On the basis of the grain size analysis, there is formed the grain size distribution, i.e. the value of the cumulative grain size distribution as a function of the grain size. From the grain size distribution, there is mathematically calculated the content of a desired element and/or mineral by means of a calibration model, which calibration model describes the dependence between the element and/or mineral content and grain size distribution. In the calculation of the content, there can generally be used any mathematical function $G(F(x))$, where $F(x)$ is the measured cumulative or differential grain size distribution, or a parameter calculated from the distribution; the shape of the function G can be defined by calibration, by applying multivariate statistical methods. Generally a calibration model is formed as data based, by extracting from the measured slurry a statistically representative number of single samples, by analyzing the element and/or mineral contents of the samples in a laboratory and by matching the grain size distributions obtained by statistical methods, for example by Multilinear Regression (MLR), Principal Components Regression (PCR) or Partial Least Squares regression (PLS) analysis, with the laboratory measurement results. The content to be analyzed can be either element or mineral content, depending on the process in question and the need for process control. Said defined content value is used in the process control by adjusting the process in the desired direction on the basis thereof, by adjusting for instance the contents of the feed, product or side product contents.

The results shown in FIGS. 2a, 2b and 2c illustrate the invention, together with the example described below. The example refers to the concentration of sedimentary phosphate ore, in which case the applied separation process is gravity separation and classification carried out in cyclones. The task is to recover apatite minerals from the ore, which apatite minerals are in the separation process feed clearly coarser than silicate minerals. In FIGS. 2a, 2b and 2c, the curve describes the cumulative grain size distribution, which is formed from the grain size analysis of the process feed, concentrate and waste. FIG. 2a illustrates the grain size distribution of the process feed, measured by an online grain size analyzer based on laser diffraction. FIG. 2b illustrates the grain size distribution of the process concentrate, and FIG. 2c illustrates the grain size distribution of the process waste. On the vertical axis in the Figures, there is illustrated the cumulative grain size quantity in percentages (% V), and on the horizontal axis, there is illustrated the diameter of a solid particle in micrometers (D μm). In the feed, nearly 100% of the apatite is over 50 micrometers in size. As regards the silicate gangue, it is again clearly finer, so that it is distinguished in the cumulative grain size distribution as a separate step in FIG. 2a. After the separation process, the concentrate (FIG. 2b) mainly consists of coarse apatite, whereas the waste (FIG. 2c) consists nearly exclusively of fine silicates. In this exemplary case, the described method proceeds as follows. When the value of the cumulative grain size distribution is obtained from the online grain size measurement as a function of the grain size, $F(x)$, for example phosphate content is calculated therefrom according to the formula % $P_2O_5 = a*F(50\ \mu m) + b$, where a and b are numerical constants. The defining of the value $F(50\ \mu m)$ is illustrated in FIG. 2a. The values of the constants a and b are defined by calibration from known samples, by matching the values of the grain size distribution $F(50\ \mu m)$ of samples with a known $P_2O_5$ content statistically, by regression analysis, with % $P_2O_5$ contents. Content measurement is utilized so that the control variables of cyclonization (the number of used cyclones, their feed flow, solid content in feed or feed pressure) are adjusted in order to get the $P_2O_5$ content in the concentrate on the required level.

For a man skilled in the art, it is obvious that the various different embodiments of the invention are not restricted to the above described examples, but may vary within the scope of the accompanying claims.

The invention claimed is:

1. A method of controlling a mineral separation process comprising:
   receiving a flow of finely divided particle material from the mineral separation process,
   extracting a sample of said finely divided particle material from the flow,
   subjecting the sample to a grain size analysis operation,
   calculating a result of the grain size analysis operation, said result being a cumulative grain size distribution,
   determining mineral content or element content of the flow of finely divided particle material using said of cumulative grain size distribution, and
   using the determined mineral content or element content in controlling the mineral separation process.

2. A method according to claim 1, comprising calculating a value of mineral content or element content from said grain size distribution using constants defined by calibration.

3. A method according to claim 1, comprising:
   providing a plurality of samples of finely divided particle material of known mineral content or element content,
   subjecting said samples of known mineral content or element content to a grain size analysis operation,
   calculating a result of the grain size analysis operation for each sample of known mineral content or element content, said result being a cumulative grain size distribution for the respective sample, and
   deriving a calibration model that relates cumulative grain size distribution of said samples of known mineral content or element content to mineral content or element content,
   and wherein the step of determining mineral content or element content of the flow of finely divided particle material comprises applying said calibration model to the cumulative grain size distribution of the sample extracted from the flow of finely divided particle material.

4. A method according to claim 1, comprising subjecting said sample to a laser diffraction method for determining grain size distribution.

5. A method according to claim 1, comprising subjecting said sample to an ultrasonic absorption method for determining grain size distribution.

6. A method according to claim 1, comprising subjecting said sample to an optical image analysis method for determining grain size distribution.

7. A method according to claim 1, comprising using said information in controlling the mineral separation process for obtaining an optimal feed.

8. A method according to claim 1, comprising using said information in controlling the mineral separation process for obtaining an optimal product.

9. A method according to claim 1, comprising using said information in controlling the mineral separation process for obtaining an optimal by-product.

10. A method according to claim 1, wherein the mineral separation process is flotation.

11. A method according to claim 1, wherein the mineral separation process is gravity separation.

12. A method according to claim 1, wherein the mineral separation process is magnetic separation.

13. A method according to claim 1, wherein the mineral separation process is electrostatic separation.

14. A method according to claim 1, wherein the mineral separation process is classification.

15. A method of recovering valuable minerals from mined material, comprising:
mechanically comminuting the mined material to provide a finely divided feed material,
supplying the feed material to a mineral separation process in which the feed material is divided into a product stream and a waste stream,
extracting a sample of said feed material, said product stream, or said waste stream,
subjecting the sample to a grain size analysis operation,
calculating a result of the grain size analysis operation, said result being a cumulative grain size distribution,
determining mineral content or element content of the feed material, the product stream or the waste stream, as the case may be, using said cumulative grain size distribution, and
using the determined mineral content or element content in controlling the mineral separation process.

16. A method according to claim 15, comprising extracting a sample of said product stream and using said information in controlling the mineral separation process.

17. A method according to claim 15, comprising extracting a sample of said waste stream and using said information in controlling the mineral separation process.

18. A mineral separation process comprising:
receiving a supply of finely divided feed material,
dividing the feed material into a product stream and a waste stream,
extracting a sample of said feed material, said product stream, or said waste stream,
subjecting the sample to a grain size analysis operation,
calculating a result of the grain size analysis operation, said result being a cumulative grain size distribution,
determining mineral content or element content of the feed material, the product stream or the waste stream, as the case may be, using said the cumulative grain size distribution,
using the determined mineral content or element content in controlling the step of dividing the feed material into the product stream and the waste stream.

19. A method according to claim 18, comprising extracting a sample of said product stream and using the determined mineral content or element content in controlling the step of dividing the feed material into the product stream and the waste stream.

20. A method according to claim 18, comprising extracting a sample of said waste stream and using the determined mineral content or element content in controlling the step of dividing the feed material into the product stream and the waste stream.

21. A method according to claim 18, comprising extracting a sample of said feed material and using the determined mineral content or element content in controlling the step of dividing the feed material into the product stream and the waste stream.

22. A method according to claim 18, comprising:
providing a plurality of samples of finely divided particle material of known mineral content or element content,
subjecting said samples of known mineral content or element content to a grain size analysis operation,
calculating a cumulative grain size distribution for each sample of known mineral content or element content as a result of the grain size analysis operation,
deriving a calibration model that relates cumulative grain size distribution of said samples of known mineral content or element content to mineral content or element content, and
calculating a value of mineral content or element content of the flow of finely divided particle material by applying said calibration model to the cumulative grain size distribution of the sample extracted from the flow of finely divided particle material.

23. A method according to claim 15, comprising:
providing a plurality of samples of finely divided particle material of known mineral content or element content,
subjecting said samples of known mineral content or element content to a grain size analysis operation,
calculating a cumulative grain size distribution for each sample of known mineral content or element content as a result of the grain size analysis operation,
deriving a calibration model that relates cumulative grain size distribution of said samples of known mineral content or element content to mineral content or element content, and
calculating a value of mineral content or element content of the flow of finely divided particle material by applying said calibration model to the cumulative grain size distribution of the extracted sample of said feed material, said product stream, or said waste stream.

\* \* \* \* \*